(12) United States Patent
Wang et al.

(10) Patent No.: US 7,723,084 B2
(45) Date of Patent: May 25, 2010

(54) FIBROUS PROTEIN-IMMOBILIZATION SYSTEMS

(75) Inventors: Ping Wang, Hudson, OH (US); Darrell Reneker, Akron, OH (US); Hongfei Jia, Akron, OH (US); Guangyu Zhu, Troy, NY (US)

(73) Assignee: The University of Akron, Akron, OH (US)

(*) Notice: Subject to any disclaimer, the term of this patent is extended or adjusted under 35 U.S.C. 154(b) by 1022 days.

(21) Appl. No.: 10/519,216

(22) PCT Filed: Jun. 18, 2003

(86) PCT No.: PCT/US03/19197

§ 371 (c)(1),
(2), (4) Date: Sep. 1, 2005

(87) PCT Pub. No.: WO03/106655

PCT Pub. Date: Dec. 24, 2003

(65) Prior Publication Data

US 2006/0094096 A1 May 4, 2006

Related U.S. Application Data

(60) Provisional application No. 60/389,537, filed on Jun. 18, 2002.

(51) Int. Cl.
*C12N 11/16* (2006.01)
*C07K 17/00* (2006.01)

(52) U.S. Cl. ..................... 435/174; 530/350
(58) Field of Classification Search .......... 435/174; 530/350

See application file for complete search history.

(56) References Cited

U.S. PATENT DOCUMENTS

| | | | |
|---|---|---|---|
| 3,925,157 A | | 12/1975 | Hamsher |
| 3,985,616 A | | 10/1976 | Weaver et al. |
| 3,985,617 A | | 10/1976 | Yugari et al. |
| 4,008,126 A | | 2/1977 | Keyes |
| 4,141,857 A | | 2/1979 | Levy et al. |
| 4,338,401 A | * | 7/1982 | Cremonesi .............. 435/178 |
| 4,371,612 A | * | 2/1983 | Matsumoto et al. ........ 435/44 |
| 4,539,294 A | | 9/1985 | Metcalfe et al. |
| 4,727,030 A | | 2/1988 | Ishimura et al. |
| 4,978,619 A | | 12/1990 | Kajiwara et al. |
| 5,482,996 A | | 1/1996 | Russell et al. |
| 5,914,367 A | | 6/1999 | Dordick et al. |
| 6,099,960 A | * | 8/2000 | Tennent et al. .......... 428/367 |
| 6,667,099 B1 | * | 12/2003 | Greiner et al. .......... 428/398 |

OTHER PUBLICATIONS

Greco E et al (2006) CpG oligodeoxynucleotides induce Ca2+-dependent phospholipase D activity leading to phagolysosome maturation and intracellular mycobacterial growth inhibitions in monocytes. Biochem Biophys Res Comm, vol. 347, pp. 963-969.*
Iyer et al. , Abstracts of Papers, 221st ACS national meeting, San Diago, CA, United States, Apr. 1-5, 2001, ANYL-035.*
"Enzyme-Carrying Polymeric Nanofibers Prepared via Electrospinning for Use as Unique Biocatalysts" by Dept. of Chemical Eng., American Chemical Society (2002).
"Enzyme-Carrying Polymeric Nanofibers Prepared via Electrospinning for Use as Unique Biocatalysts" by Dept. of Chemical Eng., American Chemical Society (2002) Jia et al., Biotechnol. Prog. 2002, 18, 1027-1032.

* cited by examiner

*Primary Examiner*—Chih-Min Kam
(74) *Attorney, Agent, or Firm*—Roetzel & Andress; Joseph J. Crimaldi

(57) ABSTRACT

The present invention provides a fibrous protein-immobilization system composition comprising a fiber comprising fiber-forming material, and a protein attached to the fiber-forming material.

17 Claims, No Drawings

FIBROUS PROTEIN-IMMOBILIZATION SYSTEMS

This application is a 371 of PCT/US03/19197, filed Jun. 18, 2003, which claims the benefit of U.S. Provisional Application 60/389,537 filed Jun. 18, 2002, which are hereby incorporated by reference.

FIELD OF THE INVENTION

This invention relates to fibrous protein-immobilization systems and methods for their synthesis and use.

BACKGROUND OF THE INVENTION

Enzymatic biotransformations have been pursued extensively for many important chemical processing applications such as chemical production, drug synthesis, pollutant degradation, and petroleum refining because of their unparalleled selectively and mild reaction conditions. In many cases, however, low catalytic efficiency and stability of enzymes have been seen as barriers for the development of large-scale operations to compete with traditional chemical processes.

In practice, almost all large-scale industrial operations preferably employ immobilized enzymes because they afford easy recycling, feasible continuous operations, and simplified product purification. Many methods have been developed to incorporate enzymes into a variety of organic and inorganic solid supports, entrap enzymes in hollow fibers or microcapsules, and cross-link enzymes via covalent bonds. Among other factors, the structure of the support materials has a great impact on the performance of the immobilized enzymes. Nonporous support materials, to which enzymes are attached at the surfaces, are subject to minimum diffusional limitations. However, enzyme loading per unit mass of support is usually low. Alternatively, high enzyme loading can be achieved with porous materials such as membranes, gel matrices, and porous materials. Porous materials, however, suffer much greater diffusional limitation. For example, the value of effectiveness factor ($\eta$, which measures the ratio of apparent heterogeneous reaction rate to homogeneous reaction rate) for $\alpha$-chymotrypsin entrapped in polyacrylamide hydrogel was reported to be ~0.3; for $\alpha$-chymotrypsin incorporated into hydrophobic plastics, $\eta$ was below 0.1; for cross-linked $\alpha$-chymotrypsin, $\eta$ was below $10^{-3}$. Higher $\eta$ values are possible for the same immobilized enzyme but used for nonaqueous reactions, mostly due to the relatively slower reaction rates involved there.

The reduction in size of support materials can effectively improve the efficiency of immobilized enzymes. In some cases, such at in the case of surface attachment on non-porous materials, smaller particles have been shown to provide relatively higher enzyme loading per unit mass. For porous materials, smaller particles are subject to much reduced diffusional resistance because of a shortened path of diffusion.

Many studies on the use of micrometer sized materials have been conducted. However, it has only been recently that even smaller scale materials have been studied. In these newer studies, nanoparticles have been used as carriers or supports for enzyme immobilization. The effective enzyme loading on nanoparticles can be very high, and a large surface area per unit mass is also available to facilitate reaction kinetics. It will be appreciated that the enzymes are attached to the nanoparticles.

While the use of nanoparticles provide excellent results in terms of balancing the contradictory issues of surface area, diffusion resistance, and effective enzyme loading, their ability to be dispersed in reaction solutions and their subsequent recovery for reuse are dauntingly difficult.

There is, therefore, still a need for immobilizing enzymatic catalysts by employing substrates that have the benefits of nanosized materials, e.g., have relatively high enzyme loading capability, have large surface area, and have minimal diffusional limitations, but yet are easily recoverable for reuse or continuous use.

SUMMARY OF THE INVENTION

The present invention provides a fibrous protein-immobilization system composition comprising a fiber comprising fiber-forming material, and a protein attached to the fiber-forming material.

The present invention further provides a method for synthesizing a fibrous protein immobilization system comprising the steps of synthesizing a fiber comprising a fiber-forming material, and attaching a protein to the fiber-forming material.

The present invention advantageously overcomes problems in the prior art by immobilizing proteins via attaching them to the fiber-forming material of a fiber. Advantages provided by the fibrous protein-immobilization system include: relatively high surface area per unit mass of the fibrous protein-immobilization system, relatively reduced diffusional resistance, relatively high protein loading upon the fiber, and relative ease of recovery. Further, enzyme activity and stability is significantly enhanced with the fibrous protein-immobilization systems.

Fibrous protein-immobilization systems can be employed in a variety of applications including:

A. Industrial bioprocessing for chemical production, drug synthesis, pollutant degradation, fuel processing, and the like.

B. Constructing bioactive filtration materials that can be used to prepare higher performance barriers, fabrics; constructing filters that employ enzymes for degrading volatile organic pollutants in order to improve air quality; and degrading chemical warfare agents such as nerve gas.

C. Producing biosensors that can be used for clinical, environmental, and military applications.

D. Constructing energy devices by employing redox enzymes into electro-conductive fibers (such as those of polyaniline). The fibers can then be used to construct bio-electrodes that generate electrical power using bio-materials including sugar, alcohol, and urea as energy sources.

DETAILED DESCRIPTION OF THE ILLUSTRATIVE EMBODIMENTS

Fibrous protein-immobilization systems (fibrous systems) comprise proteins that are attached to the fiber-forming materials of a fiber. The term "attached" refers to two substances being linked to each other by a chemical bond, e.g., a protein attached to a fiber-forming material. Fibrous systems are synthesized by attaching proteins to fiber-forming material before or after the fiber-forming material is processed into a fiber. Proteins can be attached to a fiber-forming material directly or indirectly. Direct attachment occurs where a chemical bond exists between a protein and a fiber-forming material, and indirect attachment occurs where an inert coupling agent links a protein to a fiber-forming material.

Both natural and synthetic proteins can be employed in fibrous systems. Non-limiting examples of useful proteins include enzymes, hormones, toxins, antibodies, antigens, lectins, structural proteins, signal proteins, transport proteins, receptors, and blood factors. Proteins generally include at least one functional group that can react with a corresponding functional group on a fiber-forming material or coupling agent and thereby create a point of attachment. For example, most naturally occurring proteins include at least one of the following functionalities: amine [(RNH$_2$), R(NH), C(NH), and (NH$_2$)], sulfhydryl (RSH), carboxyl (RCOOH), and phenol (RC$_6$H$_4$OH). Enzymes are preferably employed in fibrous protein-immobilization systems, and examples of preferred enzymatic functional groups are:

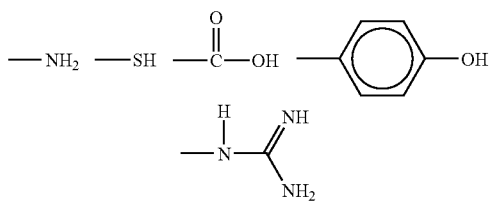

Enzymes can catalyze chemical reactions. Some preferred enzymes employed in fibrous systems include those having biochemical activities such as chymotrypsin, cytochrome C, trypsin, subtilisin, horseradish peroxidase, soybean peroxidase, and glucose oxidase. Especially preferred enzymes are α-chymotrypsin, β-galactosidase, and chloroperoxidase.

Some enzymes catalyze reactions because of the amino acid residues that form their polypeptide chains; an example is pancreatic ribonuclease. Other enzymes, however, require an additional chemical component called a cofactor for catalytic activity. The cofactor can be an inorganic compound or element, such as Fe$^{2+}$, Mn$^{2+}$, or Zn$^{2+}$ ions, or it may be a complex organic molecule called a coenzyme; coenzymes act as carriers of specific functional groups. Some enzymes require both a coenzyme and one or more metal ions for activity. In some enzymes, the coenzyme or metal ion is only loosely and transiently bound to the protein, but in others it is tightly and permanently bound via covalent chemical bonds, in which case it is called a prosthetic group. A complete catalytically active enzyme together with its coenzyme or metal ion is called a holoenzyme. The protein part of the holoenzyme is called the apoenzyme.

The protein loading of a fibrous protein-immobilization system can be from about 0.01% to about 99% weight of the fibrous system. Preferably, protein loading is from about 0.1% to about 10% weight of the fibrous system, and more preferably protein loading is from about 1% to about 10% weight of the fibrous system.

Fibers employed in the present invention can comprise a variety of fiber-forming materials, which includes any polymer that can be dissolved in a solvent. Preferably, a polymer that retains its mechanical strength while swollen with solvents, reactants, or reaction products is employed as a fiber-forming material because of its durability under conventional chemical process operating conditions. More preferably, polymeric fiber-forming materials are employed in synthesizing fibers that can be crosslinked into a strong network.

Fiber-forming material can comprise chemical functionalities that allow the fiber-forming material to attach to either a protein or coupling agent. For instance, a fiber-forming material could be a functionalized polymer that derives from either a natural or synthetic polymer. Examples of useful fiber-forming materials include, but are not limited to, polymers such a nylon, polyacrylonitrile (PAN), polyesters, polyurethanes, silanes, or copolymers thereof. Useful synthetic polymers that can be employed as fiber forming materials are: plastics, solid powders, resins, and waxes that are linear and soluble in a solvent such as chloroform, dimethylformide, or toluene. A polymeric fiber-forming material that is preferably employed is polystyrene. Polymeric fiber-forming materials can be synthesized or modified using conventional techniques so that they comprise an appropriate functional group that will allow them to attach to a protein or coupling agent.

Any functional group that will allow a fiber-forming material to attach to a coupling agent or protein can be employed in the fibrous system. Non-limiting examples of useful functional groups on fiber-forming materials include hydroxy groups (—OH), amine groups (RNH$_2$ and (R$_2$NH), sulfhydryl groups (RSH), carboxyl groups (—COOH), and aldehyde groups [—C(O)H].

Non-limiting examples of preferred functional groups for fiber-forming materials are:

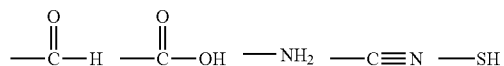

Linear polymers are examples of fiber-forming materials that can be modified to include a functional group. Linear polymers include but are not limited to: homopolymers and copolymers of α-olefins, α-β-ethylenically unsaturated carboxylic acids, vinyl aromatics, ethyl ethers, and combinations thereof. Exemplary α-olefins include: ethylene, propylene, pentene 1-butene, 1-hexene, 4methyl-1 pentene, 1-octene, 1-decene, or combinations thereof. Exemplary α-β-ethylenically unsaturated carboxylic acids include: acrylic acid, methacrylic acid. Exemplary vinyl aromatics include styrene. Exemplary ethyl ethers include: ethylene glycol, vinyl ethyl ether, vinyl acetate, and methyl methacrylate. Preferred polymers are: polyethylene glycol, polystyrene, poly(methyl methacrylate), poly(vinyl acetate), and poly(vinyl ethyl ether).

Without undue experimentation, a person of ordinary skill in the art can select and employ a fiber-forming material having a functional group that will react with a corresponding functionality on a protein or coupling agent and thereby attach the two together.

The fiber-forming material loading of a fibrous system can be from about 0.01% to about 99% weight of the fibrous system. Preferably, fiber-forming material loading is from about 0.1% to about 90% weight of the fibrous system, and more preferably protein loading is from about 1% to about 80% weight of the fibrous system.

Coupling agents can be employed in fibrous systems to serve as a link between fiber-forming materials and proteins. Useful coupling agents include compounds that are preferably inert except for having at least two reactive functional groups wherein at least one of the coupling agent's functional groups can react with a functionality on a protein and at least another of its functional groups can react with a functionality on a fiber-forming material.

Non-limiting examples of preferred coupling agents are:

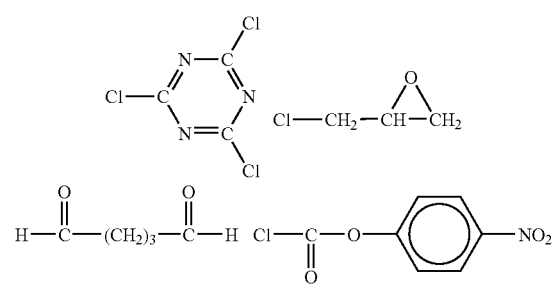

-continued

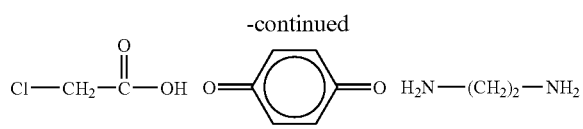

The loading of coupling agents that can be employed in a fibrous protein-immobilization system can make up from about 0.0001% to about 50% of the total weight of the fibrous system. Preferably, coupling agents make up from about 0.001% to about 1% of the total weight of the fibrous system, and more preferably coupling agents make up from about 0.001% to about 0.1% of the total weight of the fibrous system.

Various conventional techniques that can be used to form fibers can be employed in synthesizing fibrous catalyst-immobilization systems, however electrospinning is preferred. The technique of electrospinning of solutions containing fiber-forming material, is known and has been described in a number of patents as well as in the general literature. Electrospinning involves introducing a solution into an electric field, whereby the solution is caused to produce fibers that tend to be drawn to an electrode. While being drawn from the solution, the fibers usually harden, which may involve mere cooling (e.g., where the liquid is normally solid at room temperature), chemical hardening (e.g., by treatment with a hardening vapor), or evaporation of solvent (e.g., by dehydration). The product fibers may be collected on a suitably located receiver and subsequently stripped from it. Electrospinning can produce fibers from a great variety of fiber-forming materials, and the fibers can have diameters greater than or equal to about two nanometers.

When electrospinning is employed, any solvent in which a fiber-forming material is soluble can be used to prepare solutions that can be used to synthesize fibrous systems. Therefore, when preparing solutions comprising fiber-forming materials, persons of ordinary skill in the art can employ appropriate solvents based on the solubility characteristics of fiber-forming material(s) without undue experimentation.

The percent concentration of a solvent in a solution for electrospinning can be from about 0% to about 99% volume of the solution. Preferably solvent is employed from about 0% to about 85% volume of the solution. More preferably, solvent is employed from about 0% to about 75% volume of the solution.

The percent concentration of fiber-forming material in a solution for electrospinning can be from about 0% to about 99% volume of the solution. Preferably fiber-forming material is employed from about 0% to about 85% volume of the solution. More preferably, fiber-forming material is employed from about 0% to about 75% volume of the solution.

Proteins can be attached to fiber-forming materials directly or indirectly. Direct attachment occurs where a protein chemically bonds to a fiber-forming material, and indirect attachment occurs where a coupling agent links a protein to a fiber-forming material.

In order to directly attach a protein to a fiber-forming material, a chemical bond must form between the two. Direct attachment is preferably achieved by presenting a protein to a fiber-forming material via a solution comprising proteins. Fiber-forming materials are preferably immersed or dissolved into the solution for a sufficient time that allows the chemical functionalities on the fiber-forming material to bond to the proteins. Where two immiscible solutions are employed, one comprising proteins and the other comprising fiber-forming material, agitation or convention emulsion techniques are preferably employed. Additionally, proteins can also be presented to fiber-forming materials via mist or using other conventional methods.

Where proteins in solution are being directly or indirectly attached to fiber-forming material in solution and that has not yet been processed into a fiber, the solution comprising proteins preferably has a concentration of proteins ranging from about 0.001% to about 50% weight of the solution. Preferably, the concentration of proteins in solution ranges from about 0.01% to about 10% weight of solution. More preferably, the concentration of proteins in solution ranges from about 0.01% to about 1% weight of solution.

When proteins are being directly attached to fiber-forming material that has been processed into a fiber, the fiber is preferably immersed in a solution comprising proteins wherein the concentration of proteins in the solution can be from about 0.001% to about 50% by weight of the solution. Preferably the concentration of proteins in solution is from about 0.001% to about 10% weight of the solution, and more preferably the concentration of proteins in solution is from about 0.01% to about 1% weight of the solution.

Indirect attachment of a protein to a fiber-forming material requires that a coupling agent serve as a link between the two. The protein and fiber-forming material preferably possess chemical functionalities that will chemically bond to the coupling agent. And where a coupling agent is employed, the coupling agent is preferably first attached to the fiber-forming material and then the protein. The preferred sequence of indirect attachment can be achieved by immersing or dissolving a fiber-forming material into a solution comprising coupling agents for a sufficient time that allows the fiber-forming materials to bond to the coupling agents. Following this first attachment, the coupling agent(s) are then preferably introduced into a separate solution comprising proteins for a sufficient time that allows the coupling agent's functionalities to chemically bond to the proteins.

Other alternative methods for indirect attachment can include various sequences of attachment involving solutions of fiber-forming material, coupling agents, proteins, and combinations thereof. Where two solutions are immiscible, agitation and conventional emulsion techniques are preferably employed.

Where coupling agents in solution are being attached to fiber-forming material in solution and that has not been processed into a fiber, the solution comprising coupling agents preferably has a concentration of coupling agents ranging from about 0.001% to about 50% weight of the solution. Preferably, the concentration of coupling agents in solution ranges from about 0.01% to about 1% weight of solution. More preferably, the concentration of coupling agents in solution ranges from about 0.01% to about 0.1% weight of solution.

In order to attach coupling agents to fiber-forming materials that have been processed into a fiber, the fiber is preferably immersed in a solution comprising coupling agents wherein the concentration of coupling agents in solution ranges from about 0.001% to about 100% by weight of the solution. Preferably the coupling agents have a concentration in the solution ranging from about 0.001% to about 1% weight of the solution, and more preferably the coupling agents have a concentration ranging from about 0.01% to about 0.1% weight of the solution.

Where a single solution comprises coupling agents and proteins in order to attach the two to each other, the concentration of coupling agents in solution can range from about 0.001% to about 50% weight of the solution. Preferably the concentration of coupling agents in the solution ranges from about 0.01% to about 1% weight of the solution, and more preferably the concentration of coupling agents in the solution ranges from about 0.01% to about 0.1% weight of the solution.

Where a single solution comprises coupling agents and proteins in order to attach the two to each other, the concentration of proteins in solution can range from about 0.001% to about 90% by weight of solution. Preferably proteins are in solution at a concentration ranging from about 0.01% to about 20% by weight of solution, and more preferably the concentration of proteins in the solution ranges from about 0.01% to about 10% by weight of solution.

Where proteins in solution are being attached to coupling agents in solution and two solutions are required because the coupling agents and proteins are insoluble in the same solvent, the concentration of proteins in solution can range from about 0.001% to about 90% by weight of solution. Preferably proteins are in solution at a concentration ranging from about 0.01% to about 20% by weight of solution, and more preferably the concentration of proteins in the solution ranges from about 0.01% to about 10% by weight of solution.

Additionally, where two solutions are required because the coupling agents and proteins are insoluble in the same solvent, the concentration of coupling agents in solution can range from about 0.0001% to about 100% by weight of solution. Preferably coupling agents are in solution at a concentration ranging from about 0.01% to about 10% by weight of solution, and more preferably the concentration of coupling agents in the solution ranges from about 0.1% to about 10% by weight of solution.

Where a cofactor is required for an enzyme to display catalytic activity, the cofactor can be presented to a fibrous system via fluid. In an alternative method, the cofactor can be presented to the enzyme by attaching the cofactor to a fiber-forming material by similar methods described hereinabove regarding the attachment of fiber-forming materials and proteins. Where cofactors are attached to the fiber-forming materials of fibers, enzymes can be presented to the cofactors by either attaching them to the fiber or incorporating them into a fluid that contacts the cofactor.

Where a cofactor is presented via fluid to a fibrous system, the concentration of cofactors in solution ranges from about 0.0001% to about 50% weight of solution. Preferably, the concentration of cofactors in solution ranges from about 0.001% to about 10% by weight of solution. More preferably, the concentration of cofactors in solution ranges from about 0.001% to about 10% by weight of solution.

Where a fluid is employed as a means to present an enzyme to a cofactor that is attached to the fiber-forming material of a fiber, the concentration of enzymes in solution can range from about 0.001% to about 50% weight of solution. Preferably, the concentration of enzymes in solution ranges from about 0.01% to about 20% weight of solution. More preferably, the concentration of enzymes in solution ranges from about 0.01% to about 10% by weight of solution.

In order to demonstrate the practice of the present invention, the following examples have been prepared and tested. The examples should not, however, be viewed as limiting the scope of the invention. The claims will serve to define the invention.

EXAMPLES

Samples of functionalized polystyrene were first synthesized in a manner well known in the art. In particular, polymerization of styrene was conducted in a 20 ml scintillation vial under $N_2$. In a typical procedure, 0.1 g of 2-2'-azobis[2-methyl-N-(2-hydroxyethyl) propionanide ("propionamide") was first dissolved into 4 ml N,N-dimethylformamide (DMF). The solution was then mixed with 5 ml styrene and 1 ml toluene. The vial was purged with $N_2$ and incubated in water bath at 72° C. for 24 hours. The reaction was stopped via pouring the reaction solution into 50 ml of methanol to precipitate polystyrene. The precipitate was further washed by 25 ml methanol for at least 3 times to remove unreacted styrene and initiator. The molecular weight of polystyrene was measured by GPC using a PLgel MIXED column (Polymer Laboratories, MA) with chloroform as the mobile phase.

Polystyrene was then functionalized in a typical manner as follows. Typically, 0.5 g polystyrene and 12.2 mg 4(dimethylamino)-pyridine (DMAP) were dissolved in 8 ml toluene and cooled to 4° C. in a 20 ml scintillation vial. The reaction was initiated by adding 2 ml of 0.01 M 4-nitrophenyl chloroformate (NPC) (in anhydrous methylene chloride) under stirring. The reaction was allowed to last 5 hours before centrifugation to remove the precipitate of 4-dimethylaminopyridine hydrochloride. The supernatant containing polystyrene attached with nitrophenyl ending groups CPS-NPh) was precipitated and washed with methanol. The final product was dried by blowing $N_2$.

Fibers were then made by electrospinning. To that end, a polymer solution was prepared at room temperature by dissolving PS-NPh in a mixture of methyl ethyl ketone (MEK) and DMF (v:v=1:1) containing 0.5%-wt LiCl. The polymer solution was electrospun following a similar procedure as reported previously (60) with an electric field strength of 0.75 KV/cm. A Teflon capillary tube with an orifice diameter of 0.2 mm was used as the jet. Fibers were collected on glass slides, stainless meshes or aluminum foil for different studies such as SEM analysis and enzyme immobilization. The weight of supporting materials was measured before and after the collection to monitor the net weight of accumulated fibers.

Enzyme immobilization was accomplished as follows. Nanofibers collected on stainless mesh were immersed in borate buffer solution (pH 8.2) containing α-chymotrypsin (typically 5 mg/ml). The reaction system was slightly shaken at room temperature for 36 hours, followed by washing the fibers with pH 8.2 buffer and deionized water till no absorbance at 280 nm was observed in the washing solution. The fibers were finally dried by purging $N_2$ and stored at 4° C.

The amount of active α-chymotrypsin on nanofibers was determined by active site titration. Typically, certain amount of nanofibrous enzyme (~1 mg) was added to 3 ml 4-methylumbelliferyl p-trimethylammonium cinnamate chloride (MUTMAC) solution (pH 7.5 borate buffer), and the product concentration was measured using fluorescence (excitation at 360 nm, emission at 450 nm) on a luminescence spectrometer (Model LS50B, Perkin-Elmer Analytical Instruments). Fibers were removed from the solution by filtration using 0.22 μm PTFE filter before spectrophotometric measurements.

The hydrolytic activity of α-chymotrypsin was measured using n-succinyl-ala-ala-pro-phe p-nitroanilide (SAAPPN) as substrate in pH 8.2 borate buffer. In a typical measurement for native enzyme, 1 ml of 0.8 mM substrate solution was mixed with 10 μl of enzyme solution (0.01~0.3 mg/ml) in a 1 ml cuvette, and the concentration of the hydrolysis product, p-nitroaniline, was monitored by the absorbance at 410 nm. The hydrolysis reaction with nanofibrous enzyme was conducted in 20 ml vials. Nanofibers with known weight (~0.1 mg) were added to 4 ml substrate solution under stirring and the absorbance at 410 nm was measured after the removal of the fibers. The time course of the hydrolysis reaction catalyzed by the nanofibrous enzyme was obtained with at least 5 reactions started at the same time under the same reaction conditions, but were stopped and analyzed for product concentration at different times (2~20 min).

The transesterification activity of α-chymotrypsin in organic solvents was measured at room temperature in hexane or isooctane containing n-acetyl-$_L$-phenylalanine propyl ester (APEE) (concentration ranged from 2.5 to 30 mM) and 0.5 M n-propyl alcohol. The solvents received from the supplier were stored with 3 Å molecular sieves for at least 24 h before being used. Typically 5 mg of native α-chymotrypsin or 1 mg of nanofibrous enzyme was added to 10 ml reaction solution to initiate the reaction. The reaction system was shaken at 200 rpm, and the enzyme was removed by filtration using 0.22 μm PTFE syringe filter. The product concentration was monitored by using Gas Chromatography equipped with a FID detector and a RIX-5 capillary column (0.25 mm×0.25 μm×10 m, Shimadzu). A temperature gradient from 100° C. to 190° C. at a heating speed of 20° C./min, followed by 5-min retention at 190° C. was used. The initial reaction rate for the formation of n-acetyl-$_L$-phenylalanine propyl ester (APPE) was calculated using data collected before the conversion reached 5%.

Samples of native and nanofibrous α-chymotrypsin were then incubated in methanol at room temperature (22° C.). The incubation was stopped at desired times by purging $N_2$ to remove methanol. The hydrolysis activities were then measured using SAAPPN as substrate in aqueous buffer, according to the procedure described above.

Based upon the foregoing, it will be appreciated that polystyrene with a molecular weight of 200 kDa was synthesized via bulk polymerization, followed by functionalization with nitrophenyl chloroformate. The functionalized polystyrene was then electrospun into nanofibers for use as support materials for enzyme immobilization. It has been reported that beaded fibers were often generated in many electrospinning processes. The beaded structure, which reduces the surface area/mass ratio of the fibers, is not desired for enzyme immobilization as concerned in this work. Initially, spinning of the functionalized polystyrene resulted in the formation of beads on the fibers. However, the addition 0.5%-wt of LiCl, which introduces additional charges to the polymer solution, effectively suppressed the generation of beads. The diameter of fibers was controlled by varying the concentration of polystyrene. Fibers with diameters ranging from 120 nm to ~1 μm were prepared and examined for the immobilization of α-chymotrypsin.

The attachment of α-chymotrypsin to polystyrene nanofibers was achieved by immersing the fibers into an aqueous buffer containing the enzyme. The covalent binding was evident in that the enzyme retained on the fiber after extensive wash with buffer and deionized water. The amount of enzyme attached to the fibers was detected via active site titration. For large-scale applications, high enzyme loading is always desired to reduce the size of bioreactors. The enzyme loading on nanofibers is expected to be high considering the great surface area provided by such a structure. A theoretical enzyme loading, which varies with the diameter of the nanofibers, can be calculated by assuming monolayer coverage of the outer surface of the fibers. The measured enzyme loading generally increases as the diameter of fibers decreases, following the same trend as predicted by theoretical calculations. An enzyme loading of 1.4%-wt was observed with fibers of 120 nm, corresponding to 27.4% monolayer coverage of the fiber.

The stoichiometric enzyme loading of α-chymotrypsin on polystyrene (200 kDa) is 11%-wt (assuming 1:1 coupling between the polymer and enzyme), which is higher than the enzyme loading needed for a monolayer coverage of the fibers examined. That implies that it is possible to achieve a monolayer coverage of the nanofibers with the α-chymotrypsin-polystyrene system. Several factors may contribute to low enzyme loading. First, the hydrolysis of the functional group, nitrophenyl group, may compete with the immobilization reaction for active sites on the surface of fibers, and may ultimately lead to the limited attachment of enzyme molecules. This adverse effect can be reduced by increasing the concentration of enzyme in the reaction solution, and higher enzyme loading was achieved in this way. Second, α-chymotrypsin may undergo autolysis under the immobilization conditions, and the resulted amino acid fragments may also compete for active sites on the fiber. Another imaginable factor is the availability of functional groups attached to the polymer. It is possible that certain fraction of the functional ending groups are embedded in the fiber and are not exposed to the outer surface. In this regard, reducing the diameter of the fibers will increase the exposure of the functional groups and thus improve the enzyme loading.

The hydrolytic activity of the nanofibrous α-chymotrypsin was measured in aqueous solution, and it accounted 65% of that of native α-chymotrypsin for the same hydrolysis reaction. This is a quite high activity as compared with other forms of immobilization. The apparent activities of immobilized enzymes are usually much lower than the homogeneous activities of native enzymes, particularly in the case of enzymes immobilized into porous materials because of the relatively higher diffusional resistance involved there. For example, the effectiveness factor of α-chymotrypsin immobilized in porous materials was mostly found in the range of 0.1~30%. In the case of nanofibrous enzyme, even though the enzyme loading is similar to or even higher than those achieved with porous materials, the enzyme is exposed to the outer surface and much less diffusional resistance can be expected. Other factors, however, may become predominant in limiting the activity of the nanofibrous α-chymotrypsin. For example, it has been demonstrated that the covalent binding of α-chymotrypsin to solid supports led to certain conformational changes of the enzyme molecules, and such conformational changes in turn adversely affected the intrinsic reaction kinetic parameters of the enzyme. Accordingly, it is believe that the 35% activity loss of the nanofibrous enzyme is mainly caused by the structural changes due to the chemical attachment of polymers.

In contrast to what observed in aqueous solutions, the apparent activities of nanofibrous α-chymotrypsin in organic solvents were found much higher than that of native α-chymotrypsin. Nanofibrous α-chymotrypsin exhibited activities that are up to 5670 times higher than native α-chymotrypsin suspended in the same organic solvents. The activity enhancement achieved by the nanofibrous enzyme is even higher than those observed for α-chymotrypsin solubilized in the organic solvents via ion-pairing, in which case the highest enhancement was ~2400-fold. This was an unexpected observation because the ion-paired enzymes provide a homogeneous reaction configuration, which should afford the enzyme the upper limiting activity in organic solvents.

It has been well demonstrated that water has a great impact on the activities of enzymes in organic solvents. For example, the activities of alcohol oxidase, mushroom polyphenol oxidase and horse liver alcohol dehydrogenase in organic solvents were found greatly increased upon the addition of water (up to 10%-v/v). In tests with the nanofibrous α-chymotrypsin of the present invention, the addition of 0.1%-v/v water to organic solvents also led to a significant increase in the enzymes' activity. However, the increase in native enzyme's activity appeared to be much more dramatic than nanofibrous enzyme, such that the relative activity enhancement (ratio of activity of nanofibrous enzyme to native enzyme) decreased noticeably with increase in water content. One consideration is that the added water may not only lead to the hydration of native enzymes in organic media, but may also improve their dispersion thus resulted in higher apparent activities. In the case of nanofibrous enzymes, which have been dispersed well in organic solvents through the fibers, the addition of water may only impact enzyme activity through the hydration mechanism.

Covalent binding of enzymes to solid supports usually improve the enzymes' stability against inactivation induced by structural denaturation. Such a stabilization effect was also observed with the nanofibrous α-chymotrypsin. Both native and nanofibrous enzymes were first conditioned in anhydrous methanol at room temperature. Methanol was selected due to its well-known ability to denature proteins. Upon the removal of methanol by evaporation, the enzymes were reconstituted into aqueous solutions and their hydrolytic activities were measured. The half-life time of the nanofibrous enzyme was found to be over 18-fold longer than that of the native enzyme.

In another embodiment, Table I presents recipes for three solutions that were electrospun to produce fibers. Pure methylethylketone (MEK) was employed as the solvent, and the weight percentage of the fiber-forming material, polystyrene nitrophenylchloroformate (PST-NPC), was altered to yield fibers of different sizes.

TABLE I

Solution Recipe

| Trial | PST-NPC % by Weight of Solution | MEK | PST-NPC |
|---|---|---|---|
| 1 | 15 | 0.5 ml | 0.0710 g |
| 2 | 20 | 0.5 ml | 0.1006 g |
| 3 | 25 | 0.5 ml | 0.1342 g |

PST-NPC can be synthesized using conventional techniques. MEK was obtained from Sigma Chemicals, Australia.

Enzyme attachment to the electrospun fibers was achieved by immersing the fibers in a solution comprising alpha chymotrypsin in a borate buffer having a pH of 8.2. The concentration of alpha chymotrypsin in the solution was 5 milligrams per milliliter of buffer. The fibers were immersed in the solution for approximately 2 days. α-Chymotrypsin was obtained from Sigma Chemicals, Australia.

Various modifications and alterations that do not depart from the scope and spirit of this invention will become apparent to those skilled in the art. This invention is not to be duly limited to the illustrative embodiments set forth herein.

What is claimed is:

1. A fibrous protein-immobilization system composition comprising:
    a nanofiber comprising a fiber-forming material; and
    a protein covalently attached to the fiber-forming material, wherein the nanofiber includes at least one functional group suitable to permit the attachment of the protein, wherein the at least one function group is contained within a portion of the fiber-forming material, and wherein the fiber-forming materials are linear polymers selected from the group consisting of homopolymers and copolymers of α-olefins, α,β-ethylenically unsaturated carboxylic acids, vinyl aromatics, ethyl ethers, and combinations thereof.

2. The fibrous protein-immobilization system composition, as set forth in claim 1, wherein the protein is attached indirectly to the fiber-forming material by an inert coupling agent.

3. The fibrous protein-immobilization system composition, as set forth in claim 2, wherein the protein includes at least one functional group that can react with a corresponding functional group on the inert coupling agent.

4. The fibrous protein-immobilization system composition, as set forth in claim 1, wherein the protein is a natural or synthetic protein.

5. The fibrous protein-immobilization system composition, as set forth in claim 4, wherein the protein is selected from the group consisting of enzymes, hormones, toxins, antibodies, antigens, lectins, structural proteins, signal proteins, transport proteins, receptors, and blood factors.

6. A fibrous protein-immobilization system composition comprising:
    a nanofiber comprising a fiber-forming material; and
    a protein covalently attached to the fiber-forming material, wherein the nanofiber includes at least one functional group suitable to permit the attachment of the protein, wherein the at least one function group is contained within a portion of the fiber-forming material, wherein the protein is attached directly to the fiber-forming material, and wherein the fiber-forming material is selected from the group consisting of nylons, polyesters, polyurethanes, silanes, or copolymers thereof.

7. The fibrous protein-immobilization system composition, as set forth in claim 6, wherein the protein includes at least one functional group that can react with the at least one functional group on the nanofiber comprising fiber-forming material.

8. A fibrous protein-immobilization system composition comprising:
    a nanofiber comprising a fiber-forming material; and
    a protein covalently attached to the fiber-forming material, wherein the nanofiber includes at least one functional group suitable to permit the attachment of the protein, wherein the at least one function group is contained within a portion of the fiber-forming material, wherein the protein is an enzyme selected from the group consisting of chymotrypsin, cytochrome C, trypsin, subtilisin, horseradish peroxidase, soybean peroxidase, and glucose oxidase, and wherein the fiber-forming material is selected from the group consisting of nylons, polyesters, polyurethanes, silanes, or copolymers thereof.

9. A fibrous protein-immobilization system composition comprising:
    a nanofiber comprising a fiber-forming material; and
    a protein covalently attached to the fiber-forming material; wherein the nanofiber includes at least one functional group suitable to permit the attachment of the protein; wherein the at least one function group is contained within a portion of the fiber-forming material, wherein the protein is contained within the fiber-forming material, and wherein the fiber-forming material is selected from the group consisting of nylons, polyesters, polyurethanes, silanes, or copolymers thereof.

10. A method for synthesizing a fibrous protein-immobilization system comprising the steps of:
    synthesizing a nanofiber comprising a fiber-forming material, wherein the nanofiber includes at least one functional group suitable to permit the attachment of a protein and wherein the at least one function group is contained within a portion of the fiber-forming material; and attaching the protein covalently to the fiber-forming material, and wherein the fiber-forming materials are linear polymers selected from the group consisting of homopolymers and copolymers of α-olefins, α,β-ethylenically unsaturated carboxylic acids, vinyl aromatics, ethyl ethers, and combinations thereof.

11. The method of claim 10, wherein the protein is attached to the fiber-forming material after the fiber-forming material is synthesized into a nanofiber.

12. The method of claim 10, wherein the step of attaching includes attaching the protein to a coupling agent and the coupling agent to the fiber-forming material.

13. A method for synthesizing a fibrous protein-immobilization system comprising the steps of:

synthesizing a nanofiber comprising a fiber-forming material, wherein the nanofiber includes at least one functional group suitable to permit the attachment of a protein, wherein the at least one function group is contained within a portion of the fiber-forming material, and wherein the fiber-forming materials are linear polymers selected from the group consisting of homopolymers and copolymers of α-olefins, α,β-ethylenically unsaturated carboxylic acids, vinyl aromatics, ethyl ethers, and combinations thereof; and attaching the protein covalently to the fiber-forming material, wherein the protein is attached to the fiber-forming material before the fiber-forming material is synthesized into a nanofiber.

14. A method for synthesizing a fibrous protein-immobilization system comprising the steps of:

synthesizing a nanofiber comprising a fiber-forming material, wherein the nanofiber includes at least one functional group suitable to permit the attachment of a protein, wherein the at least one function group is contained within a portion of the fiber-forming material, and wherein the fiber-forming materials are linear polymers selected from the group consisting of homopolymers and copolymers of α-olefins, α,β-ethylenically unsaturated carboxylic acids, vinyl aromatics, ethyl ethers, and combinations thereof; and attaching the protein covalently to the fiber-forming material, wherein the step of synthesizing includes electrospinning a solution of the fiber-forming material to produce the nanofiber.

15. A method for synthesizing a fibrous protein-immobilization system comprising the steps of:

synthesizing a nanofiber comprising a fiber-forming material, wherein the nanofiber includes at least one functional group suitable to permit the attachment of a protein, wherein the at least one function group is contained within a portion of the fiber-forming material, and wherein the fiber-forming materials are linear polymers selected from the group consisting of homopolymers and copolymers of α-olefins, α,β-ethylenically unsaturated carboxylic acids, vinyl aromatics, ethyl ethers, and combinations thereof; and attaching the protein covalently to the fiber-forming material, wherein the protein is an enzyme and the method further comprises the step of attaching a cofactor to the fiber-forming material or the step of contacting the enzyme with a cofactor in a fluid.

16. The method of claim 15, wherein the enzyme is contacted to the cofactor in a fluid.

17. A method for synthesizing a fibrous protein-immobilization system comprising the steps of:

synthesizing a nanofiber comprising a fiber-forming material, wherein the nanofiber includes at least one functional group suitable to permit the attachment of a protein and wherein the at least one function group is contained within a portion of the fiber-forming material; and attaching the protein covalently to the fiber-forming material, wherein the protein is contained within the fiber-forming material, and wherein the fiber-forming material is selected from the group consisting of nylons, polyesters, polyurethanes, silanes, or copolymers thereof.

* * * * *